United States Patent
Shelley et al.

(10) Patent No.: US 7,431,918 B2
(45) Date of Patent: Oct. 7, 2008

(54) ANHYDROUS ANTIPERSPIRANT COMPOSITION

(76) Inventors: Walter B. Shelley, 21171 River Rd., Grand Rapids, OH (US) 43522; Harry J. Hurley, 4119 Echo Valley La., Newtown Square, PA (US) 19073

( * ) Notice: Subject to any disclaimer, the term of this patent is extended or adjusted under 35 U.S.C. 154(b) by 343 days.

(21) Appl. No.: 11/372,906

(22) Filed: Mar. 10, 2006

(65) Prior Publication Data

US 2007/0212313 A1  Sep. 13, 2007

(51) Int. Cl.
- *A61Q 15/00* (2006.01)
- *A61K 33/06* (2006.01)
- *A61K 8/00* (2006.01)
- *A61K 8/02* (2006.01)

(52) U.S. Cl. .................. 424/65; 424/400; 424/401; 424/696

(58) Field of Classification Search .................. 424/65, 424/400, 401, 696
See application file for complete search history.

(56) References Cited

U.S. PATENT DOCUMENTS

| | | | |
|---|---|---|---|
| 3,088,874 A | 5/1963 | Geary et al. | |
| 4,552,753 A | 11/1985 | Elm et al. | |
| 4,724,138 A * | 2/1988 | Duffy et al. | 424/63 |
| 6,642,285 B1 * | 11/2003 | Bohner | 523/115 |
| 2003/0161858 A1 * | 8/2003 | Lidgren | 424/423 |

FOREIGN PATENT DOCUMENTS

EP  1557159 A1  7/2005

OTHER PUBLICATIONS

International Search Report for PCT Patent Application No. PCT/US05/38459, dated Aug. 17, 2007.
International Search Report for PCT Patent Application No. PCT/US07/61193, dated Oct. 5, 2007.
Shelley, W.B., Hurley, H.J.: Studies on topical antiperspirant control of axillary hyperhidrosis. Acta Derm Venereol (Stockholm) 55: 241-260, 1975.
Shelley, W.B., Hurley, H.J., Nichols, A.C.: Axillary Odor: Experimental Study of the role of bacteria, apocrien sweat and deodorants. AMA Arch. Dermatol. Syph. 68: 430-436, 1953.
Laden, K., editor; Antiperspirants and Deodorants. 2$^{nd}$ Edition. Revised and Expanded. Marcel Dekker, Inc. New York, 1999, pp. 1-16, 59-214, 233-282, 327-375.

* cited by examiner

*Primary Examiner*—Shelley A. Dodson
(74) *Attorney, Agent, or Firm*—Schnader Harrison Segal & Lewis, LLP

(57) ABSTRACT

An antiperspirant composing calcium sulfate hemihydrate in an anhydrous state or in an anhydrous composition and method of treating hyperhidrosis.

19 Claims, No Drawings

ANHYDROUS ANTIPERSPIRANT COMPOSITION

FIELD OF INVENTION

This invention relates to a composition particularly suitable for treating localized hyperhidrosis.

BACKGROUND OF THE INVENTION

Control of excessive perspiration by use of a topical formulation has long been a medical and social goal. Excessive sweating accounts for intertrigo, infection, dermatitis, and friction blisters of wet soles. It also results in disability for typing and writing due to dripping palms, being handicapped in sporting events from facial sweat, and having a compromised grip on baseball bats, tennis racquets, and basketballs. On the social side, hyperhidrosis induces the embarrassment of wet armpit clothing, gustatory sweating and auriculotemporal facial sweating (Frey's syndrome), and varied patches of nevoid localized sweating. All intertriginous areas, including fat folds and toe-webs, are susceptible to harm by unevaporated trapped sweat which induces maceration and leads to secondary bacterial and fungal infections. Add to this the cost of dry cleaning clothing and shoe replacement. Total localized control of sweating by topical means has thus been a long term medical objective.

The first commercial antiperspirant was introduced approximately 100 years ago. It was an aqueous-alcoholic solution of aluminum chloride hexahydrate with an effectiveness now estimated to be 60-70%. Through the century, the effectiveness of commercial antiperspirants has dropped to the 30-55% range due to the industry replacing aluminum chloride hexahydrate with weaker, more alkaline, less irritating salts of aluminum. Indeed, today the FDA approves the label "antiperspirant" for any product that reduces axillary sweating by 20% in 50% of users—and no product can be labeled "stops sweating" (Laden K., Ed., Antiperspirants and Deodorants $2^{nd}$ Edition, 1999).

Numerous commercial over-the-counter and prescription products are useful for controlling excessive sweating in localized areas such as the axilla. Nearly all depend on the well-known antiperspirant action of aluminum chloride hydrate and its cognate derivatives, including the fellow metallic antiperspirant zirconium salts.

SUMMARY OF THE INVENTION

The present invention provides an effective alternative antiperspirant that contains no aluminum or zirconium salts. This invention controls hyperhidrosis topically by the application of a unique and safe chemical—calcium sulfate hemihydrate—in an anhydrous system.

DESCRIPTION OF INVENTION

The present invention embodies the hither-to unrecognized antiperspirant effect of topical calcium sulfate hemihydrate in an anhydrous system.

Calcium sulfate hemihydrate, $CaSO_4\text{-}1/2H_2O$ or $(CaSO_4)_2\text{-}H_2O$, which has a formula weight of 145.15, is a white compound. It has the unique property of reacting with sweat, i.e. water, to form a hard crystalline film of the dihydrate of calcium sulfate in an exothermic reaction. This focal reaction specifically occludes the sweat pores, thereby counteracting hyperhidrosis. The formulations of calcium sulfate hemihydrate are sensitive to water, and hence must be anhydrous and protected from excessive atmospheric water vapor.

Calcium sulfate hemihydrate is available commercially as a fine white hygroscopic powder kept in closed containers. In an illustrative embodiment of the invention, this antiperspirant agent is applied directly as a powder or from a compacted stick. Alternately, it is applied as an impalpable powder from 5 to 25 micron incorporated into an anhydrous carrier vehicle. The formulation preferably should be dispensed in a sealed container or applicator, but other means of dispensing and application are within the spirit and scope of the invention.

The calcium sulfate hemihydrate may be applied directly as a powder from a powder container or an aerosol unit with appropriate protective shield to guard against inhalation. Alternatively, it may be made into a stick applicator, consisting of compacted powder with or without an excipient to prevent crumbling. The stick is preferably oval, measuring, for example, 1.5 inches by 0.75 inches. It may be dispensed in a standard plastic holder with a knurled screw at the base for advancement.

In another embodiment of the invention, the calcium sulfate hemihydrate is incorporated by trituration into any of a number of anhydrous vehicles. The carrier vehicle is anhydrous castor oil from which trace water has been eliminated by the addition of molecular sieve 3A, either in powder or granular form.

Other satisfactory vehicles include anhydrous ethyl alcohol, dehydrated castor oil (Castung R 103 G-H) or safflower oil. Glycerol, petroleum and aqueous agents are not satisfactory. The calcium sulfate hemihydrate is preferably triturated into a paste, cream, or suspension, wherein the ratio of antiperspirant agent to vehicle is 1:1 on a weight/volume basis, although it can be varied from a ratio as high as 1.5:1 or as low as 1:10. Calcium sulfate hemihydrate is insoluble in all common solvents. The only solubilizer is tetrahydrofuran, a compound too toxic for human use.

In the manufacture of the invention a dry atmosphere is preferable since calcium sulfate hemihydrate is hygroscopic and thereby converted to inactive calcium sulfate dihydrate.

The compacted stick can be molded by appropriate compression machinery. A powder processor (Micronizer R. Jet Mill Sturdevant, Hanover, Mass.) may be used to grind the active ingredient to a particle size of 3 to 35 micron, ideally about 5 micron. The powder is added in a homogenizer to the selected vehicle, all operations being carried out in ambient dry air or water-free nitrogen gas. As desired, pigments, fragrance, and necessary modifiers, as for example cyclomethicones, may be added.

The product may be packaged in an applicator appropriate for a cream, paste, gel, suspension, or stick. When the formulation is liquid the standard roll-on unit is satisfactory. The pure stick formulation has the advantage of simplicity and ease of use.

In a further embodiment of the invention, emulsifiers, structurants or a combination thereof are added to the composition to form a cream or gel.

The anhydrous antiperspirant composition of the invention may be applied topically to the axillae, intertriginous areas, forehead, palms, and soles in amounts covering the skin site in question.

The compositions act specifically on the sweat pore when applied to dry skin. The are activated by sweat.

FORMULATION EXAMPLE I

| Calcium sulfate hemihydrate | 30.0 grams |
| --- | --- |
| 5 micron powder | |
| Castor Oil USP | 30 ml |

FORMULATION EXAMPLE II

| Calcium sulfate hemihydrate | 30 grams |
| --- | --- |
| Ethyl alcohol, absolute | 30 ml |
| Dispense in Roll On and shake before use | |

FORMULATION EXAMPLE III

| Calcium sulfate hemihydrate | 30 grams |
| --- | --- |
| Dehydrated Castor Oil | 30 ml |

FORMULATION EXAMPLE IV

Calcium Sulfate Hemihydrate

Compressed in stick mold shape. Active powder released by friction of application.

While the invention has been described by illustrative embodiments, additional advantages and modifications will occur to those skilled in the art. Therefore, the invention in its broader aspects is not limited to specific details shown and described herein. Modifications, for example, to the relative concentrations and types of components may be made without departing from the spirit and scope of the invention. Accordingly, it is intended that the invention not be limited to the specific illustrative embodiments, but be interpreted within the full spirit and scope of the appended claims and their equivalents.

What is claimed is:

1. An antiperspirant product characterized by a composition consisting of calcium sulfate hemihydrate in an anhydrous state incorporated into an anhydrous vehicle.

2. The composition of claim 1 wherein the composition is in powder form.

3. The composition of claim 1 wherein the composition is compacted into a stick form.

4. The composition of claim 1 wherein the calcium sulfate hemihydrate particle size is in the range of about 3 microns to about 35 microns.

5. The composition of claim 4 wherein the calcium sulfate hemihydrate particle size is in the range of about 5 microns to about 25 microns.

6. The composition of claim 1 wherein the anhydrous vehicle is selected from the group consisting of castor oil CP, dehydrated castor oil, anhydrous ethyl alcohol, and safflower oil.

7. The composition of claim 1 wherein a ratio of the calcium sulfate hemihydrate to the anhydrous vehicle is from about 1:10 by weight/volume to about 1.5:1 by weight/volume.

8. A method of preparing an antiperspirant consisting essentially of:
   micronizing calcium sulfate hemihydrate to an impalpable powder in a size from about 3 microns to about 35 microns; and
   packaging the powder in an anhydrous state in aerosol unit.

9. A method of preparing an antiperspirant consisting essentially of:
   micronizing calcium sulfate hemihydrate in a size from about 3 microns to about 35 microns; and
   triturating the calcium sulfate hemihydrate into an anhydrous vehicle.

10. The method of claim 9, wherein the anhydrous vehicle is selected from the group consisting of castor oil CP, dehydrated castor oil, anhydrous ethyl alcohol, and safflower oil.

11. The method of claim 9 further comprising:
    adding emulsifiers, structurants or a combination thereof to the anhydrous vehicle to form a cream.

12. The method of claim 9 further comprising:
    adding emulsifiers, structurants or a combination thereof to the anhydrous vehicle to form a gel.

13. The method of claim 9 further comprising:
    adding one or more pigments to the anhydrous vehicle.

14. The method of claim 9 further comprising:
    adding a fragrance to the anhydrous vehicle.

15. The method of claim 9 further comprising:
    adding a cyclomethicone to the anhydrous vehicle.

16. A method of treating hyperhidrosis comprising applying a composition consisting essentially of calcium sulfate hemihydrate in an anhydrous state incorporated into an anhydrous vehicle to the affected area.

17. The method of claim 16 wherein the anhydrous vehicle is selected from the group consisting of castor oil CP, dehydrated castor oil, anhydrous ethyl alcohol, and safflower oil.

18. The method of claim 16 wherein the particle size of the calcium sulfate hemihydrate is in the range of about 3 microns to about 35 microns.

19. The method of claim 16 wherein a ratio of the calcium sulfate hemihydrate to the anhydrous vehicle is from about 1:10 by weight/volume to about 1.5:1 by weight/volume.

* * * * *